(12) United States Patent
Park et al.

(10) Patent No.: US 8,247,538 B2
(45) Date of Patent: Aug. 21, 2012

(54) PREPARATION METHOD OF RADIOISOTOPE LABELING COMPOUND USING CARBON NANOTUBE

(75) Inventors: Sang Hyun Park, Daejon (KR); Hui Jeong Gwon, Daejon (KR); Myung Woo Byun, Daejon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 1216 days.

(21) Appl. No.: 11/788,801

(22) Filed: Apr. 20, 2007

(65) Prior Publication Data

US 2008/0214797 A1 Sep. 4, 2008

(30) Foreign Application Priority Data

Aug. 28, 2006 (KR) .......................... 10-2006-0081688

(51) Int. Cl.
*C07F 13/00* (2006.01)
*C07C 279/02* (2006.01)

(52) U.S. Cl. .................. 534/14; 534/7; 534/10; 534/11; 534/12; 424/1.11; 424/1.37; 424/178.1

(58) Field of Classification Search .................. 424/1.11, 424/1.37, 178.1; 534/14
See application file for complete search history.

(56) References Cited

U.S. PATENT DOCUMENTS

| | | | |
|---|---|---|---|
| 1,944,239 A | 1/1934 | Honnef | |
| 2,167,285 A | 7/1939 | Honnef et al. | |
| 2,852,505 A | 9/1953 | Matheisel | |
| 4,088,352 A | 5/1978 | Kling | |
| 4,289,970 A | 9/1981 | Delbert | |
| 4,350,895 A | 9/1982 | Cook | |
| 4,458,167 A | 7/1984 | Leveille | |
| 4,720,840 A | 1/1988 | Anderson et al. | |
| 4,832,569 A | 5/1989 | Samuelsen et al. | |
| 5,592,818 A | 1/1997 | Williams | |
| 5,765,990 A | 6/1998 | Jones | |
| 6,648,589 B2 | 11/2003 | Williams | |
| 7,109,600 B1 | 9/2006 | Bywaters et al. | |
| 7,154,191 B2 | 12/2006 | Jansen et al. | |
| 2006/0051290 A1* | 3/2006 | Wilson et al. | 424/1.11 |
| 2006/0067941 A1* | 3/2006 | Buzatu et al. | 424/178.1 |
| 2007/0040385 A1 | 2/2007 | Uchiyama | |

FOREIGN PATENT DOCUMENTS

DE 4113624 10/1992

OTHER PUBLICATIONS

Sang Hyun Park et al. Synthesis and Radiochemical Labeling of N-(2,6-diisopropylacetanilido)-Iminodiacetic acid and it s analogues under microwave irradiation: A hepatobiliary imaging agent, QSAR Comb. Sci. 2004, 23, 868-874.*
Patrick S. Callery, et al., Tissue Distribution of Technetium-99m and Carbon . . . , J. Med. Chem., vol. 19, pp. 962-964, 1976.
Silvia S. Jurisson, et al., Potential Technetium Small Molecule . . . , Chem. Rev., vol. 99, pp. 2205-2218, 1999.
Y. Cao, et al., A Simple and Efficient Method for Radiolabeling . . . , J. Phar,. Pharmaceut. Sci., pp. 31-37, 1998.
M. Molter, et al., Properties of Various IDA Derivatives, J. Label. Compounds Padiopharm., vol. 18, pp. 56-58, 1981.
Shuang Liu, et al., 99mTc—Labeled Small Peptides as Diagnostic . . . , Chem. Rev., vol. 99, pp. 2235-2268, 1999.

* cited by examiner

*Primary Examiner* — Michael G Hartley
*Assistant Examiner* — Jagadishwar Samala
(74) *Attorney, Agent, or Firm* — Lucas & Mercanti, LLP

(57) ABSTRACT

Disclosed herein is a method for the preparation of radioisotope-labeled compounds using CNT. It comprises filling the carbon nanotube with a radioisotope; and labeling a physiologically active material with the radioisotope charged in the carbon nanotube. Taking advantage of CNT, the method can prepare a radioisotope-labeled compound invention at a high yield and in a simple manner. Also, the radioisotope, when remaining unreacted, can be recovered by the filtration of the CNT, thereby achieving the prevention of radioactive contamination and the reduction of radioactive waste. Further, the radioisotope-labeled compound is useful as a contrast medium for imaging the hepatobiliary system.

4 Claims, 4 Drawing Sheets

(a) (b)

PREPARATION METHOD OF RADIOISOTOPE LABELING COMPOUND USING CARBON NANOTUBE

CROSS-REFERENCE TO RELATED APPLICATION

This application claims the benefit of Korean Patent Application No. 10-2006-081688, filed Aug. 28, 2006 in the Korean Intellectual Property Office, the disclosure of which is incorporated herein in its entirety by reference.

BACKGROUND OF THE INVENTION

1. Field of the Invention

The present invention relates to a method for preparing a radioisotope-labeled compound using a carbon nanotube.

2. Description of the Related Art

Nuclear medicine, a branch of medicine pertaining to the diagnostic, therapeutic, and investigative use of radioactive chemical elements, requires radionuclides or pharmaceuticals labeled with radionuclides (radiopharmaceuticals) for the practice thereof. The operation of a nuclear reactor produces numerous kinds of radioisotopes. From among them, some radioactive species suitable for use in diagnosis or therapy are selected, and then processed into pharmaceuticals administrable to human bodies. Such radiopharmaceuticals guarantee defined images of lesions, readily giving information on, for example, the metastasis of cancer, which is difficult to detect using other methods.

Hepatic diseases occur particularly frequently in Asians, including Koreans. At present, liver function tests are becoming the most important diagnostic assays. Liver function tests include the use of radioisotopes to obtain nuclear scintigraphs which give important information about local lesions of the liver as well as the size, shape and gross function of the liver.

There occur diffuse diseases and local diseases in the liver. Diffuse diseases of the liver include acute hepatitis, chronic hepatitis, liver cirrhosis, injuries caused by drugs, such as alcohol, and connective tissue injury. Patients with diffuse diseases show low functioning of the liver, which can be easily detected by radionuclide imaging or nuclear scintigraphy. Hepatoma is representative of the local diseases of the liver. Imaging of the liver gives information about the location and size of the mass, as well as about the function of the liver.

Liver cancer may be caused by the metastasis of various malignant tumors as well as primary hepatoma. Success in cancer therapy depends on the control of metastasis. In images of the liver, metastatic cancer appears as a local defect. However, images of similar defects are caused by various benign lesions, normal hepatic structures, and artifacts. Therefore, the understanding of such factors is a prerequisite for reading images of the liver.

Radiopharmaceuticals for use in therapy employ radionuclides which are generally longer in half-life and weaker in penetration capability, but emit stronger radiation, sufficient to kill cells, in relation to that for use in diagnosis. Alpha ray-emitting radionuclides are excluded from radiopharmaceuticals for the reason that they are highly radioactive and difficult to purchase and to attach to other compounds. All of the radionuclides currently used in pharmaceuticals are species that emit beta rays.

As mentioned above, radiopharmaceuticals, whether for use in therapy or diagnosis, are prepared by labeling pharmaceuticals with specific radionuclides. Technetium-99m ($^{99m}Tc$) is known as the radioisotope most widely used to label radiopharmaceuticals. Technetium-99m has a half life of as short as 6 hours and emits gamma rays at 140 KeV, and thus it is not so toxic to the body. In addition, gamma radiation from the radioisotope is highly penetrative enough to obtain images. Thanks to these advantages, technetium-99m finds a broad spectrum of therapeutic and diagnostic applications in the nuclear medicine field (Sivia, S. J., John, D. L., Potential technetium small molecule radiopharmaceuticals. Chem. Rev. 99, 2205-2218, 1999; Shuang, L., Edwards, D. S., $^{99m}Tc$-Labeled small peptides as diagnostic radiopharmaceuticals. Chem. Rev. 99, 2235-2268, 1999).

Methods of labeling $^{99m}Tc$-2,6-diisopropylacetanilidoiminodiacetic acid are well known in the art (Callery, P. S., Faith, W. C., et al., 1976. Tissue distribution of technetium-99m and carbon-labeled N-(2,6)-dimethylphenylcarbamoylmethyl iminodiacetic acid. *J. Med. Chem.* 19, 962-964; Motter, M. and Kloss, G., 1981. Properties of various IDA derivatives. *J. Label. Compounds Padiopharm.* 18, 56-58; Cao, Y. and Suresh, M. R. 1998. A Simple And Efficient Method For Radiolabeling Of Preformed Liposomes. *J Pharm Pharmaceut Sci.* 1 (1), 31-37).

Basically, the conventional methods are based on the following reaction formula. In practice, a solution of $SnCl_2 \cdot 2H_2O$, serving as a reducing agent of technetium-99m, in 0.1 N HCl and 0.1 ml (10 mCi) of sodium pertechnetium were added to lyophilized 2,6-diisopropylacetanilidoiminodiacetic acid in a vial, followed by stirring at room temperature for 30 min to prepare $^{99m}Tc$-2,6-diisopropylacetanilidoiminodiacetic acid. The preparation of $^{99m}Tc$-2,6-diisopropylacetanilidoiminodiacetic acid may be realized according to the following reaction formula.

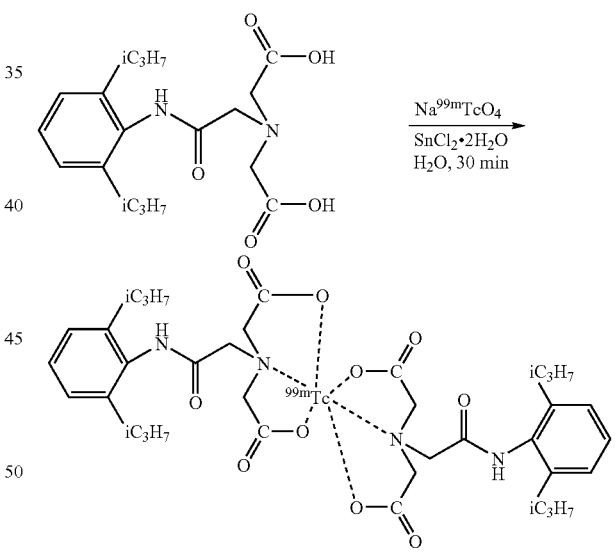

Such conventional processes of preparing radiopharmaceuticals labeled with technetium-99m can be divided into reactions between the radioisotope and a physiologically active material to be labeled and the separation of labeled compounds from unlabeled compounds.

However, conventional labeling methods are disadvantageous in terms of the long reaction time period, the exposure of the workers to radiation, and radioactive waste. Therefore, there is a need for reaction conditions under which labeling can be more simply and rapidly conducted.

Recently, novel or improved physical properties have been found in the sub-micron world on a scale as small as nanometers. Particularly, active research is focused on carbon nanotubes (CNT), which can be used as a carrier for active materials for various organic/inorganic reactions, thereby realizing novel physical properties which find valuable applications in various industries.

SUMMARY OF THE INVENTION

Leading to the present invention, intensive and thorough research into a contrast medium for use in imaging specific organs, conducted by the present inventors, resulted in the finding that carbon nanotubes are very useful in labeling physiologically active materials with radioisotopes stably and at high yield, and that when coupled with technetium-99m, a compound which is metabolized in the liver provides a high contrast ratio of images of the hepatobiliary system.

Therefore, it is an object of the present invention to provide a method for preparing a radioisotope-labeled compound using a carbon nanotube.

The above object could be accomplished by the provision of a method for preparing a radioisotope-labeled compound using a carbon nanotube, comprising filling the CNT with a radioisotope (Step 1); and labeling a physiologically active material with the radioisotope compound in the CNT (Step 2).

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
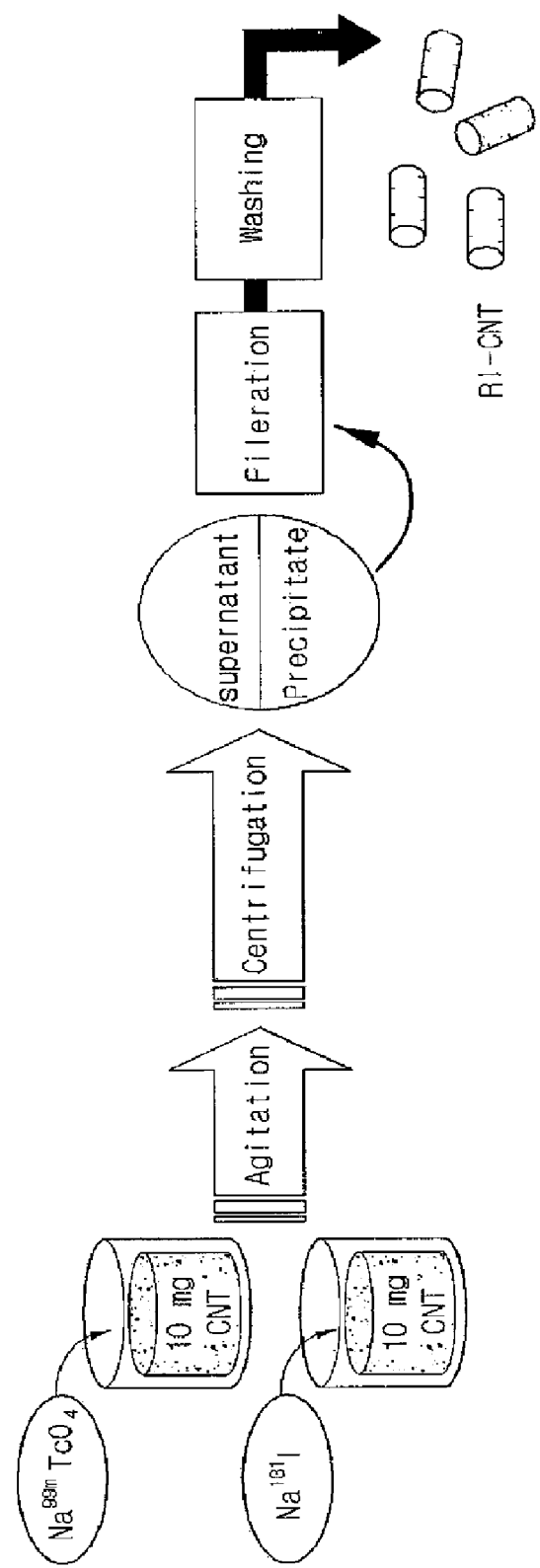
FIG. 1 is a schematic view illustrating a method for preparing a radioisotope-labeled compound using CNT in accordance with an embodiment of the present invention.

Below, a detailed description will be given of the present invention with reference to the accompanying drawings.

The present invention pertains to a method of the preparation of a radioisotope-labeled compound, starting with filling a CNT with a radioisotope.

The CNT useful in the present invention may have a single wall or a multi-wall structure.

The CNT is a commercially available one, and may be used without additional purification. Although not specifically limited, the outer diameter and length of the CNT useful in the present invention may preferably range from ones to tens of nanometers. Having a very large specific surface area and excellent physical properties, CNT, even if used in a small amount, can adsorb a large quantity of radioisotope thereon. In addition, it takes a significantly reduced time period to complete a labeling reaction by way of CNT, compared to conventional methods. Additionally, CNT reduces exposure dose and the amount of radioactive waste and guarantees a high yield for the production of radioisotope-labeled compounds.

Useful in the present invention are $^{99m}Tc$ and $^{131}I$, which have been used for the preparation of radiopharmaceuticals.

The amount of the radioisotope can be properly controlled depending on the amount of the CNT to be filled therewith or the amount of the physiologically active material to be labeled therewith. Preferably, the isotopes are used in sufficient amounts to prepare a compound labeled with $^{99m}Tc$ or $^{131}I$ at a radioactivity from approximately 5 to 30 mCi depending on the body weight of the mammal to be administered therewith.

Next, a physiologically active material is labeled with the radioisotope charged on/in the CNT.

The separation of the radioisotope from the CNT can be achieved by, but is not limited to, centrifugation into a supernatant and a pellet. The pellet is a mass of the radioisotope-filled CNTs, and is washed in accordance with the present invention. This washing step is conducted by passing the reaction mixture through a filter and washing the filtrate with water until radioactivity is detected at a very low level. The measurement of radioactivity is conducted with the washed pellet.

In accordance with an embodiment of the present invention, the physiologically active material may be 2,6-diisopropylacetanilidoiminodiacetic acid or iodobenzylguanidine. When administered orally or intravenously, the physiologically active materials 2,6-diisopropylacetanilidoiminodiacetic acid and iodobenzylguanidine are accumulated in organs, especially in the hepatobiliary system, at high concentrations.

Functioning to reduce the radioisotope, a reducing agent, selected from among ascorbic acid, cupric sulfate pentahydrate ($CuSO_4.5H_2O$), stannous chloride dehydrate ($SnCl_2.2H_2O$), and stannous sulfate ($SnSO_4$), is used to promote the labeling reaction of the physiologically active material with the radioisotope.

In accordance with another aspect, the present invention provides a contrast medium for use in imaging the hepatobiliary system, comprising the radioisotope-labeled physiologically active material prepared by way of CNT.

A better understanding of the present invention may be realized with the following examples, which are set forth to illustrate, but are not to be construed to limit the present invention.

Example 1

Preparation of $^{99m}Tc$-2,6-Diisopropylacetanilidoiminodiacetic Acid

In a tube were placed 10 mg of CNT and 10 mCi/ml of technetium-99m ($^{99m}Tc$), and the mixture was stirred for 30 min, followed by centrifugation into a supernatant and a pellet comprising the CNT filled with technetium-99m. Both were measured for radioactivity. After the filtration of the pellet through a 0.2 μm filter, the filtrate thus obtained was washed with water until radioactivity was detected at a predetermined very low level or lower. As a result, a technetium-99m-filled CNT was obtained at a yield of 75%.

1 mg of the physiologically active material 2,6-diisopropylacetanilidoiminodiacetic acid (DISIDA) was dissolved in distilled water and 0.01 mg of $SnCl_2.2H_2O$, serving as a reducing agent for technetium-99m, and the technetium-99m-filled CNTs were mixed in the solution. Stirring for 30 min at room temperature resulted in the radio-labeled compound $^{99m}Tc$-2,6-diisopropylacetanilidoiminodiacetic acid, as shown in the following Reaction Formula 1.

[Reaction Formula 1]

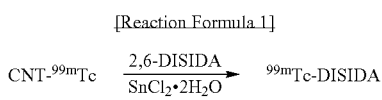

Example 2

Preparation of $^{131}$I-m-iodobenzylguanidine 10 mg of CNT and 10 mCi/ml of $^{131}$I were mixed for 30 min in a tube by stirring and centrifuged. The supernatant and the pellet comprising $^{131}$I-filled CNT were measured for radioactivity. Following the filtration of the pellet through a 0.2 μm filter, the filtrate thus obtained was washed with water until radioactivity was detected at a predetermined very low level or less. As a result, an $^{131}$I-filled CNT was obtained at a yield of 85%.

1 mg of lyophilized m-iodobenzylguanidine (mIBG), a physiologically active material, was dissolved in distilled water, and an excess of ascorbic acid, 130 μg of $CuSO_4.5H_2O$ and 0.5 mg of $SnSO_4$ were mixed together with the $^{131}$I-filled CNT in the solution. Stirring for 30 min at 80° C. resulted in the radio-labeled compound $^{131}$I-m-iodobenzylguanidine, as shown in the following Reaction Formula 2.

[Reaction Formula 2]

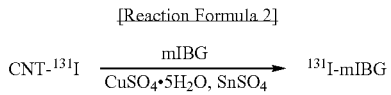

Experimental Example 1

Instant Thin Layer Chromatography (ITLC)

Radioisotope-labeled physiologically active materials were assayed for radiochemical purity as follows.

Instant thin layer chromatography was conducted to determine the radiochemical purifies of the physiologically active materials prepared in Example 1 (developing solvent, physiological saline, $R_f$=0.0; distilled water, $R_f$=0.9) and Example 2 (developing solvent, ethyl acetate:ethyl alcohol=1:1, $R_f$=0.0). The results are depicted in FIGS. 2A and 2B, respectively.

Figure 2A:
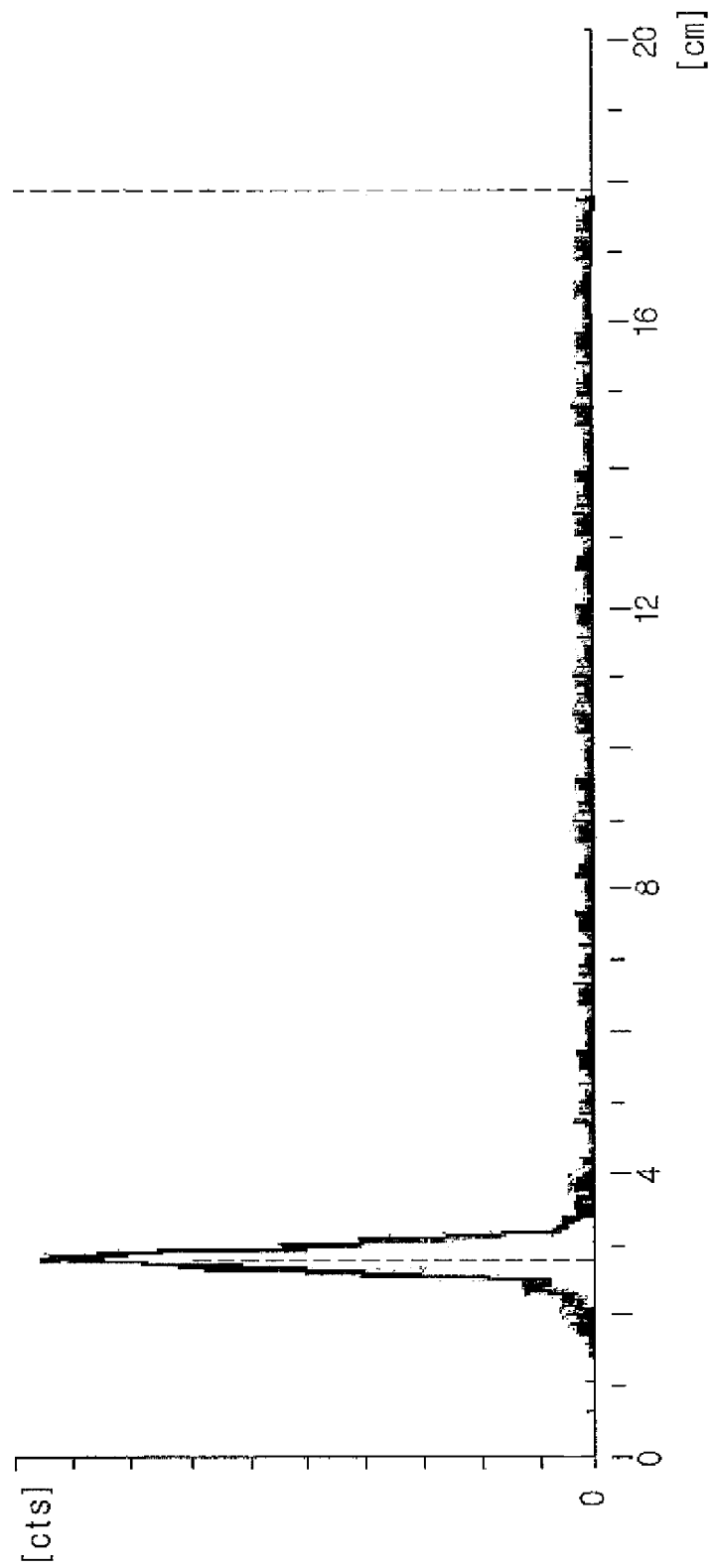
FIGS. 2A and 2B are chromatograms obtained after the instant thin layer chromatography of radioisotope-labeled compounds prepared using CNT in accordance with an embodiment of the present invention.
Figure 2B:
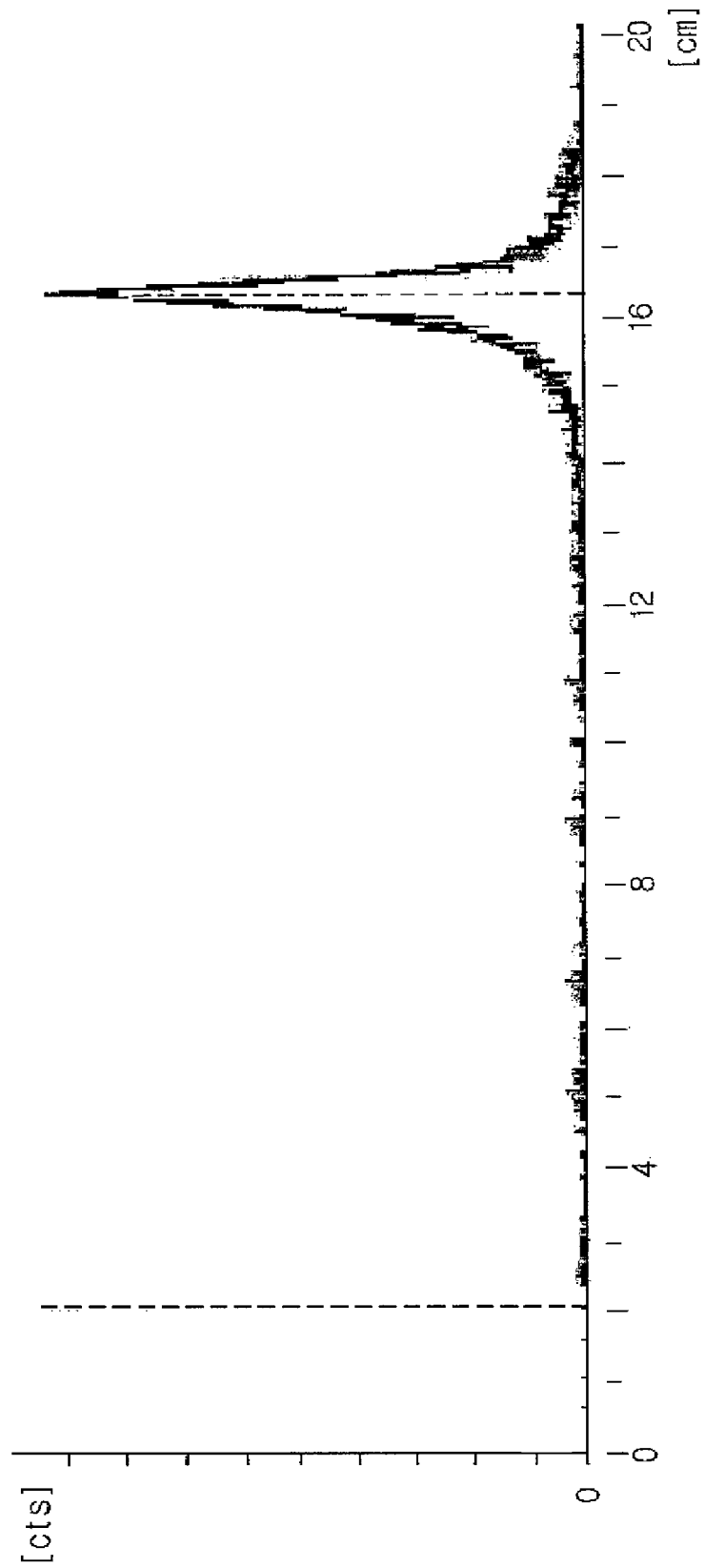

As seen in FIGS. 2A and 2B, the radiochemical purities of the radioisotope-labeled compounds of Examples 1 and 2 were read at 99% and 95%, respectively.

Experimental Example 2

Dynamic Kinetics of Radioisotope-Labeled Physiologically Active Material and Analysis Thereof The $^{99m}$Tc-2,6-diisopropylacetanilidoiminodiacetic acid prepared in Example 1 was assayed for in vivo dynamic kinetics as follows.

After 6-week-old New Zealand White male rabbits (2887.6±101.5 g, n=3) were anesthetized with ketamine and xylazine, the radioactive compound of Example 1 was injected at a dose of 100 μCi/0.1 ml into the left ear vein of each of the rabbits. All of the rabbits were placed in a pronating posture. Moving pictures were taken for 30 min of each of the rabbits using a gamma camera fitted with a low energy, multipurpose collimator while 16 still pictures were also taken at predetermined time intervals. The image analyzer was set to 140 KeV with a 20% energy window. Image data were analyzed under the dynamic procedure of a Microdelta system (Simens, USA). The static images were taken at 1.52, 3.45, 5.37, 7.30, 9.22, 11.15, 13.07, 15.00, 16.52, 18.45, 20.37, 22.30, 24.22, 26.15, 28.07 and 30 min after the injection, and the results are given in FIG. 3.

Figure 3:
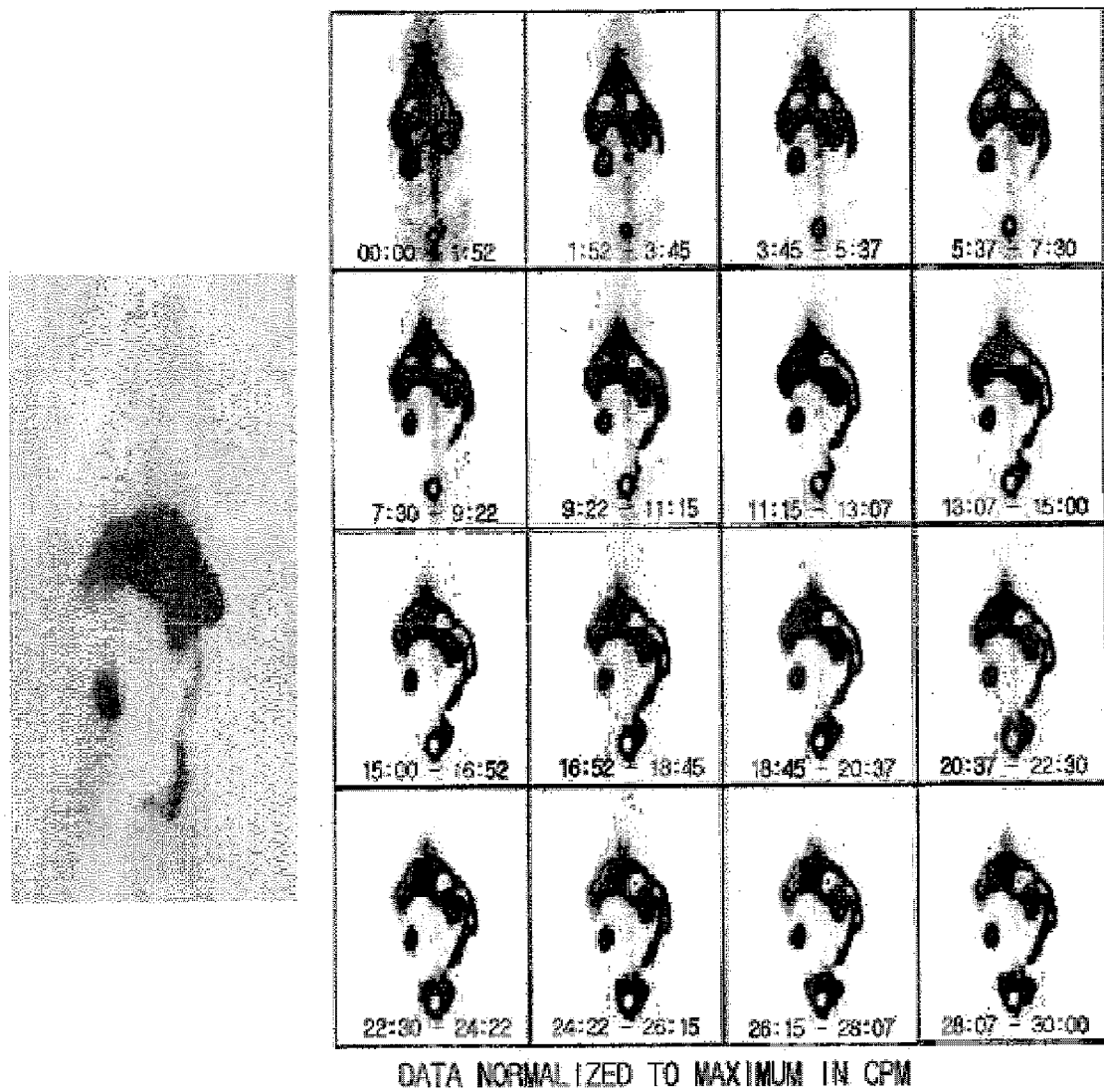
FIG. 3 shows scan images obtained from rabbits intravenously injected with a radioisotope-labeled compound prepared using CNT in accordance with an embodiment of the present invention.

As seen in FIG. 3, the contrast medium of Example 1 was detected prominently in the hepatobiliary system, with the highest concentration at the liver. Further, it is apparent that the contrast ratio between images taken of the liver and of other organs was higher when using the $^{99m}$Tc-2,6-diisopropylacetanilidoiminodiacetic acid prepared in Example 1 than conventional contrast media for imaging the hepatobiliary system.

Taking advantage of CNT, as described hitherto, the method of the present invention can prepare a radioisotope-labeled compound invention at high yield and in a simple manner. Also, the radioisotope, when remaining unreacted, can be recovered by the filtration of the CNT, thereby achieving the prevention of radioactive contamination and the reduction of radioactive waste. Further, the radioisotope-labeled compound prepared according to the method of the present invention is useful as a contrast medium for imaging the hepatobiliary system.

Although the preferred embodiments of the present invention have been disclosed for illustrative purposes, those skilled in the art will appreciate that various modifications, additions and substitutions are possible. Accordingly, the modifications, additions and substitutions should be understood as falling within the scope and spirit of the invention.

What is claimed is:

1. A method for preparing a radioisotope-labeled compound using a carbon nanotube, comprising
   (1) agitating a carbon nanotube with a radioisotope to prepare a carbon nanotube filled with a radioisotope containing an unreacted radioisotope;
   (2) washing the carbon nanotube filled with a radioisotope containing an unreacted radioisotope obtained from step (1) with water to prepare the carbon nanotube filled with a radioisotope; and
   (3) mixing the carbon nanotube filled with a radioisotope obtained from step (2) and a compound in the presence of a reducing agent to prepare a radioisotope-labeled compound,
   wherein the compound is a physiologically active material selected from the group consisting of 2,6-diisopropylacetanilidoiminodiacetic acid and iodobenzylguanidine.

2. The method as defined in claim 1, wherein the carbon nanotube has a single wall structure or a multi-wall structure.

3. The method as defined in claim 1, wherein the radioisotope is selected from among $^{99m}$Tc and $^{131}$I.

4. The method as defined in claim 1, wherein the reducing agent is selected from a group consisting of ascorbic acid, cupric sulfate pentahydrate ($CuSO_4.5H_2O$), stannous chloride dehydrate ($SnCl_2.2H_2O$), stannous sulfate ($SnSO_4$), and combinations thereof.

* * * * *